US012661333B2

(12) United States Patent (10) Patent No.: US 12,661,333 B2
Cooke et al. (45) Date of Patent: Jun. 23, 2026

(54) COMPOSITION FOR USE IN TREATMENT OF A BIOFILM IN A SUBJECT

(71) Applicant: TECHNOLOGICAL UNIVERSITY DUBLIN, Dublin (IE)

(72) Inventors: Gordon Cooke, Dublin (IE); Emma Caraher, Dublin (IE); Jonathan Brady, Dublin (IE)

(73) Assignee: TECHNOLOGICAL UNIVERSITY DUBLIN, Dublin (IE)

( * ) Notice: Subject to any disclaimer, the term of this patent is extended or adjusted under 35 U.S.C. 154(b) by 351 days.

(21) Appl. No.: 18/039,035

(22) PCT Filed: Nov. 30, 2021

(86) PCT No.: PCT/EP2021/083517
§ 371 (c)(1),
(2) Date: May 26, 2023

(87) PCT Pub. No.: WO2022/112589
PCT Pub. Date: Jun. 2, 2022

(65) Prior Publication Data
US 2024/0000739 A1 Jan. 4, 2024

(30) Foreign Application Priority Data

Nov. 30, 2020 (GB) ..................................... 2018838

(51) Int. Cl.
| | |
|---|---|
| *A61K 31/202* | (2006.01) |
| *A61K 31/7048* | (2006.01) |
| *A61K 31/7052* | (2006.01) |
| *A61P 31/04* | (2006.01) |

(52) U.S. Cl.
CPC ........ *A61K 31/202* (2013.01); *A61K 31/7048* (2013.01); *A61K 31/7052* (2013.01); *A61P 31/04* (2018.01)

(58) Field of Classification Search
None
See application file for complete search history.

(56) References Cited

U.S. PATENT DOCUMENTS

2008/0038037 A1* 2/2008 DeVore .................. B41J 2/1752
347/49
2012/0301422 A1* 11/2012 Meyer .................. A61K 9/4866
514/354

FOREIGN PATENT DOCUMENTS

KR 2019-0140677 * 6/2018 ............. A01N 31/02

OTHER PUBLICATIONS

Gupta et al., "Biofilm, pathogenesis and prevention—a journey to break the wall: a review" Arch Microbiol vol. 198 pp. 1-15, DOI 10.1007/s00203-015-1148-6 (Year: 2016).*
Chen et al., "Novel Strategies for the Prevention and Treatment of Biofilm Related Infections" Int J Mol Sci vol. 14 pp. 18488-18501, doi:10.3390/ijms 140918488 (Year: 2013).*
(Continued)

*Primary Examiner* — Andrea Olson
(74) *Attorney, Agent, or Firm* — Nixon Peabody LLP; David S. Resnick; Nicole D. Kling

(57) ABSTRACT
Provided is DHA, or a composition comprising DHA, for use in treatment of a biofilm in a subject and for use in treatment of a disease or infection associated or caused by a biofilm in a subject.

19 Claims, 3 Drawing Sheets

(56)  References Cited

OTHER PUBLICATIONS

Jiang et al., "Klebsiella pneumoniae presents antimicrobial drug resistance for β-lactam through the ESBL/PBP signaling pathway" Experimental and Therapeutic Medicine vol. 19 pp. 2449-2456, DOI: 10.3892/etm.2020.8498 (Year: 2020).*

English machine translation of KR2019-0140677, downloaded from patents.google.com (Year: 2018).*

Stando et al., "Omega-3 Polyunsaturated Fatty Acids as an Adjunct to Non-Surgical Treatment of Periodontitis" European Journal of Lipid Science and Technology vol. 121 pp. 1-6, DOI: 10.1002/ejlt.201800345 (Year: 2019).*

Hobby et al., "Exogenous fatty acids alter phospholipid composition, membrane permeability, capacity for biofilm formation, and antimicrobial peptide susceptibility in Klebsiella pneumoniae", Microbiologyopen, vol. 8, No. 2, Feb. 1, 2019.

Kumar et al., "Fatty Acids as Antibiofilm and Antivirulence Agents", Trends in Microbiology, Elsevier Science Ltd., Kidlington, GB, vol. 28, No. 9, pp. 753-768 Apr. 28, 2020.

Agarwal et al., "Biofilm-Mediated Urinary Tract Infections" Biofilms in Human Diseases: Treatment and Control, (Nov. 20, 2019), pp. 177-213.

Björnsson Sigurdur et al., "Dietary Fish Oil Supplementation Increases Survival in Mice Following Klebsiella pneumoniae Infection", Scandinavian Journal of Infectious Diseases, vol. 29, No. 5 (Jan. 8, 1997), pp. 491-493.

Brady, "The antibiofilm effects of docosahexaenoic acid." Access Miccrobiology, (Jan. 1, 2020), XP055822410, Retrieved from the Internet: URL:https://www.microbiologyresearch.org/content/journal/acmi/10.1099/acmi.mim2019.p00011.

Kim et al., "Herring Oil and Omega Fatty Acids Inhibit *Staphylococcus aureus* Biofilm Formation and Virulence", Frontiers in Microbiology, vol. 9, (Jun. 15, 2018).

Sharma et al., "Dietary supplementation with omega-3 polyunsaturated fatty acids ameliorates acute pneumonia induced by Klebsiella pneumoniae in BALB/c mice", Canadian Journal of Microbiology, NRC Research Press, CA, vol. 59, No. 7, (Jun. 30, 2013), pp. 503-510.

Sun et al., "Antibacterial and antibiofilm activities of docosahexaenoic acid (DHA) and eicosapentaenoic acid (EPA against periodontopathic bacteria", Microbial Pathogenesis, Academic Press Limited, New York, NY, US, vol. 99, (Aug. 24, 2016), pp. 196-203.

Sun Mengjun et al: "Antibacterial activities of docosahexaenoic acid (DHA) and eicosapentaenoic acid (EPA) against planktonic and biofilm growing*Streptococcus* mutans", Microbial Pathogenesis, vol. 107, Jun. 1, 2017 (Jun. 1, 2017), pp. 212-218.

* cited by examiner

1

COMPOSITION FOR USE IN TREATMENT OF A BIOFILM IN A SUBJECT

CROSS REFERENCE TO RELATED APPLICATIONS

This Application is a 35 U.S.C. § 371 National Phase Entry of International Patent Application No. PCT/EP2021/083517 filed Nov. 30, 2021, which designates the U.S. and claims benefit of foreign priority under 35 U.S.C. § 119(b) of GB Application Number 2018838.9 filed Nov. 30, 2020, the contents of which are incorporated herein in their entireties by reference.

FIELD OF THE INVENTION

The current invention relates to a method for removing or disrupting a bacterial biofilm. Specifically, the method relates to DHA, or a composition comprising DHA, for use in treatment or prevention of a biofilm in a subject and for use in treatment or prevention of a disease or infection associated or caused by a biofilm in a subject.

BACKGROUND OF THE INVENTION

Bacteria can attach to surfaces and form biofilms. A biofilm is a community of microorganisms embedded in an extracellular polymeric substance (EPS) matrix. The adherent cells tend to have a reduced growth rate and altered regulation of specific genes, compared with their freely suspended counterparts. Biofilms have a defined architecture, but every microbial biofilm is unique. The process of biofilm formation involves several key stages. The first stage involves the initial attachment of bacteria to a medical device or surface of a cell within a host. The attachment of planktonic bacteria to a surface is facilitated by the use of various adhesin molecules and cell surface appendages including pilli and fimbriae. Then microbial cells are divide rapidly while simultaneously producing an array of exopolymeric substances (EPS) which consists of extracellular proteins, various polysaccharides and extracellular DNA (eDNA). Mature biofilm formation refers to a fully developed biofilm which has successfully colonised a medical device or host tissue. At this stage, the biofilm is at its most complex as microenvironments within the biofilm form which contributes to the emergence of persister cell.

Biofilms can form on abiotic and biotic surfaces and are prevalent in both natural and hospital settings, where they are capable of surviving for extended periods of time. The ability of bacteria to form biofilms allows for recalcitrance against conventional antibiotic therapies, natural host defenses and physical stress. This has contributed to the prevalence of biofilm acquired infections (BAI) clinically, which has resulted in increased morbidity and mortality amongst patients, with immunocompromised patients being most at risk.

Various types of surfaces in a clinical setting are prone to biofilm formation and microbial infections have been observed on most, if not all, medical devices, including implants, contact lenses, urinary catheters, prosthetic heart values, pacemakers, vascular prostheses. This presents an increased risk of disease.

Biofilms are involved in numerous diseases, device and non-device associated, and often present as chronic or recurring infections. *Klebsiella pneumoniae* is a gram-negative, non-motile, encapsulated bacterium known for its ability to form biofilms. *Klebsiella* organisms are often resistant to multiple antibiotics. It is found in the normal flora of the mouth, skin and intestines but it can cause destructive changes to the human and animal lungs, specifically to the alveoli, if aspirated. Pneumonia caused by *Klebsiella* bacteria, typically in the form of bronchopneumonia and bronchitis, has a death rate of around 50%, even with antimicrobial therapy. Treatment for *Klebsiella pneumonia* is by antibiotics, such as aminoglycosides and caphalosporins, depending on the patient's health and the severity of the disease. In a healthcare setting, *Klebsiella* infections commonly occur among sick patients who are receiving treatment for other conditions. Patients who require devices such as ventilators, or catheters and patients who are taking long courses of antibiotics are most at risk.

*Enterococcus faecalis* is a gram-positive commensal bacterium inhabiting the gastrointestinal tracts of humans and other mammals. Like other species in the genus, it is found in healthy humans, but can cause life-threatening infections, such as endocarditis, sepsis and meningitis, especially in a hospital environment, where high levels of antibiotic resistance contribute to its pathogenicity. *E. faecalis* strains can form biofilms that are difficult to eradicate (Seno Y, et al., "Clinical implications of biofilm formation by *Enterococcus faecalis* in the urinary tract". Acta Med Okayama. 2005; 59:79-87).

The medical profession has been attempting to eradicate biofilm-based infections by using disinfectants and antibiotics Docosahexaenoic acid (DHA) is a poly-unsaturated fatty acid known to exhibit anti-biofilm and anti-microbial effects. (Sun et al., (2017) 'Antibacterial activities of docosahexaenoic acid (DHA) and eicosapentaenoic acid (EPA) against planktonic and biofilm growing *Streptococcus mutans*', Microbial Pathogenesis, 107(Jun), pp. 212-218 and Kim, Y. G., et al., (2018) 'Herring oil and omega fatty acids inhibit *Staphylococcus aureus* biofilm formation and virulence', Frontiers in Microbiology, 9(JUN), p. 1241). Sun et al., (2016) reported that DHA at 200 mM, exhibited cytotoxic effects when exposed to human gingival fibroblasts (HGFs) and human periodontal ligament cells (hPDLCs) for 24 and 48 hours (Sun, M., (2016) 'Antibacterial and anti-biofilm activities of docosahexaenoic acid (DHA) and eicosapentaenoic acid (EPA) against periodontopathic bacteria', Microbial Pathogenesis, 99(Oct), pp. 196-203).

Brady et al., (The antibiofilm effects of docosahexaenoic acid: Microbiology Society; 2020) discloses that their data (not shown) shows that DHA possesses anti-biofilm effects against *Klebsiella pneumoniae* and *Enterococcus faecalis* at low mM concentrations. The authors state that there is evidence (not shown) that DHA in conjunction with an antibiotic can reduce biofilm formation by these strains.

Bjornsson Sigurdur et al (Dietary fish oil supplementation increases survival in mice following *Klebsiella pneumoniae* infection, Scandinavian Journal of Infectious Diseases, vol 29, 1997) discusses a study analysing the effect of dietary fish oil supplementation on survival of mice after *Klebsiella pneumoniae* infection. The survival curve of mice fed with a fish oil enriched diet was better compared to the survival curve for mice given a corn oil enriched diet. Fish oil has long chain omega-3 fatty acid content. The authors state that increased survival may be because of the effects of fish oil on eicosanoids, cytokines and acute phase proteins and state that further studies are needed to reveal the immunopathogenesis of the effect of dietary fish oil.

Agarwal Jyotsna et al (Biofilm mediated urinary tract infections, Biofilm in Human Diseases, 2019) is a review chapter discussing biofilm mediated urinary tract infections and treatment. The authors state that biofilms play a role in catheter associated UTI (CAUTIs) and that the organisms most often contaminating these devices and developing biofilms are *Escherichia coli, Proteus mirabilis, Pseudomonas aeruginosa, Klebsiella pneumoniae, Staphylococcus epidermidis, Enterococcus faecalis* etc. The authors state that studies have recommended combination therapy for such infections rather than using single antibiotics, with macrolides being the first choice and discusses new alternative strategies for combating urinary tract infections.

However, to date no effect against *Klebsiella pneumoniae* or *Enterococcus faecalis* biofilms has been reported.

Therefore, there is a need to provide an effective means to treat biofilms comprising *Klebsiella pneumoniae* and/or *Enterococcus faecalis* in a subject. This is particularly useful for application in a hospital or clinical setting.

SUMMARY OF THE INVENTION

The current inventors have surprising found that DHA possesses strong anti-biofilm effects against *Klebsiella pneumoniae* and against *Enterococcus faecalis* even at low micromolecular concentrations. As shown in FIG. 1, DHA was capable of reducing biofilm formation by both *K. pneumoniae* NCIMB 418 and *E. faecalis* ATCC 7080 by approximately 60%. This has not been previously reported in the art.

Furthermore, the inventors have shown that DHA in combination with erythromycin is more effective at reducing biofilm formation by these strains than either treatment alone (FIG. 2). This beneficial technical effect has not been previously reported in the prior art.

An aspect of the invention relates to DHA, or a derivative thereof, for use in the treatment or prevention of a biofilm comprising *Klebsiella pneumoniae* and/or *Enterococcus faecalis* in a subject. The subject may be one with an implanted or indwelling medical device.

Preferably, DHA is provided as a composition comprising DHA. The composition may be a pharmaceutical composition. The composition may have one or more pharmaceutically excipients.

Typically, the concentration of DHA used in the method is from 1 µM to 200 µM, preferably from 6 µM to 100 µM.

In an embodiment, DHA is one with an isotopic purity of ≥90% atom % D or ≥95% or ≥98%. Typically, it is one with an isotopic purity of ≥98%.

Preferably, the method comprises administration of an antibiotic to the subject. Preferably, the antibiotic is a macrolide antibiotic. Preferably, the macrolide antibiotic is selected from azithromycin, clarithromycin, erythromycin and roxithromycin. Preferably, the macrolide is erythromycin.

DHA and the antibiotic may be administered together, or at separate times. DHA and the antibiotic may be in one composition or may be in separate compositions.

Accordingly, an aspect of the invention relates to an amount of DHA and an amount of an antibiotic for use in the treatment or prevention of a biofilm comprising *Klebsiella pneumoniae* or *Enterococcus faecalis* in a subject. The subject may be one with an implanted or indwelling medical device.

The amount of DHA and the amount of antibiotic may be administered together, or concurrently. The amount of DHA and the amount of antibiotic may be in one composition or may be in separate compositions.

The DHA and antibiotic and subject are as described herein.

An aspect of the invention relates to a composition comprising DHA for use in the treatment or prevention of a disease or condition associated with *Klebsiella pneumoniae* or *Enterococcus faecalis* biofilm formation in a subject. DHA may be as described herein.

An aspect of the invention relates to a composition comprising DHA for use in the treatment or prevention of a disease or condition associated with *Klebsiella pneumoniae* or *Enterococcus faecalis* in a subject. DHA may be as described herein.

As aspect of the invention provides a method of treatment or prevention of a biofilm comprising *Klebsiella pneumoniae* and/or *Enterococcus faecalis* in a subject, said method comprising administration of DHA to a subject. The method may further comprise administration of an antibiotic to the subject.

The embodiments and preferred features disclosed in relation to the medical use of the invention also apply to the method(s) of the invention.

Definitions and General Preferences

All publications, patents, patent applications and other references mentioned herein are hereby incorporated by reference in their entireties for all purposes as if each individual publication, patent or patent application were specifically and individually indicated to be incorporated by reference and the content thereof recited in full.

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

In this context the "disease" to be treated or prevented is any type of disease caused by or associated with *Klebsiella pneumoniae* or *Enterococcus faecalis*. In particular, it is a disease caused by or associated with a biofilm formed by, or comprising, *Klebsiella pneumoniae* or *Enterococcus faecalis*.

As used herein, the term "treatment" or "treating" refer to an intervention (e.g. the administration of an agent to a subject) which cures, ameliorates or lessens the symptoms of a disease or removes (or lessens the impact of) its cause(s). In this case, the term is used synonymously with the term "therapy". It can be manifested by a permanent or temporary improvement in the subject's condition. In this context it includes limiting and/or reversing disease progression.

As used herein the terms "prevention" or "preventing" refer to an intervention (e.g. the administration of an agent to a subject), which prevents or delays the onset or progression of a biofilm, or a disease caused by a biofilm, or the severity of said biofilm or disease, in a subject, or reduces (or eradicates) its incidence within a treated population.

As used herein, an "effective amount" or a "therapeutically effective amount" of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility, and other markers of clinical improvement. A therapeutic result need not be a complete cure.

"Pharmaceutical compositions": A further aspect of the invention relates a pharmaceutical composition comprising DHA for use according to the invention. This may be admixed with f one or more pharmaceutically acceptable excipients, particularly for human therapy. This includes diluents and carriers. The pharmaceutical compositions may be for human or animal usage in human and veterinary medicine. Examples of such suitable excipients for the various different forms of pharmaceutical compositions described herein may be found in the "Handbook of Pharmaceutical Excipients, $2^{nd}$ Edition, (1994), Edited by A Wade and PJ Weller. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical excipient can be selected with regard to the intended route of administration and standard pharmaceutical practice. Examples of suitable carriers include lactose, starch, glucose, methyl cellulose, magnesium stearate, mannitol, sorbitol and the like. Examples of suitable diluents include ethanol, glycerol and water. The pharmaceutical compositions may comprise as, or in addition to, the carrier, excipient or diluent any suitable binder(s), lubricant(s), suspending agent(s), coating agent (s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid and esters of phydroxybenzoic acid. Antioxidants and suspending agents may be also used.

As used herein, the term "biofilm" refers to a community of microorganisms in which cells stick to each other and which is enclosed in an extracellular polymeric substance (EPS) matrix. The cells must stick to a surface. The cells are enclosed in an extracellular polymeric substance (EPS) matrix. A biofilm may have one or more species. The biofilm may be one or more pellicles.

DHA or docosahexaenoic acid is an omega-3 fatty acid. Its structure is a carboxylic acid with 22-carbond chain and six cis double bonds, with the first double bond located at the third carbon from the omega end. DHA has the chemical structure shown in FIG. 3 (Calder, (2016) Docosahexaenoic acid", Annals of Nutrition and Metabolism, 69(1), pp. 8-21.)

A derivative of DHA or a metabolite may also be used. A derivative is a compound that is derives from DHA but differs by a structural modification, for example replacement of one atom or a group of atoms or a functional group with another atom or group of atoms or functional group. It is a "functional derivative" in that is has the same function, e.g. can treat or prevent a biofilm in a subject. Examples are in Yonggang Ma, et al., "DHA derivatives of fish oil as dietary supplements; a nutrition-based drug discovery approach for therapies to prevent metabolic cardiotoxicity", Expert Opin Drug Discov. 2012, Aug 7(8): 711-721.

An "immunocompromised subject" is one with a weakened immune system. The subject will have a reduced ability to fight infections and other diseases. Examples include subjects with AIDS, cancer, malnutrition, cystic fibrosis, or other genetic disorders. It may also be caused by certain medicines and treatments, such as anticancer drugs, or radiation therapy, stem cell or organ transplant.

BRIEF DESCRIPTION OF THE FIGURES

The invention will be more clearly understood from the following description of an embodiment thereof, given by way of example only, with reference to the following Figures in which.

DETAILED DESCRIPTION OF THE INVENTION

Figure 1:
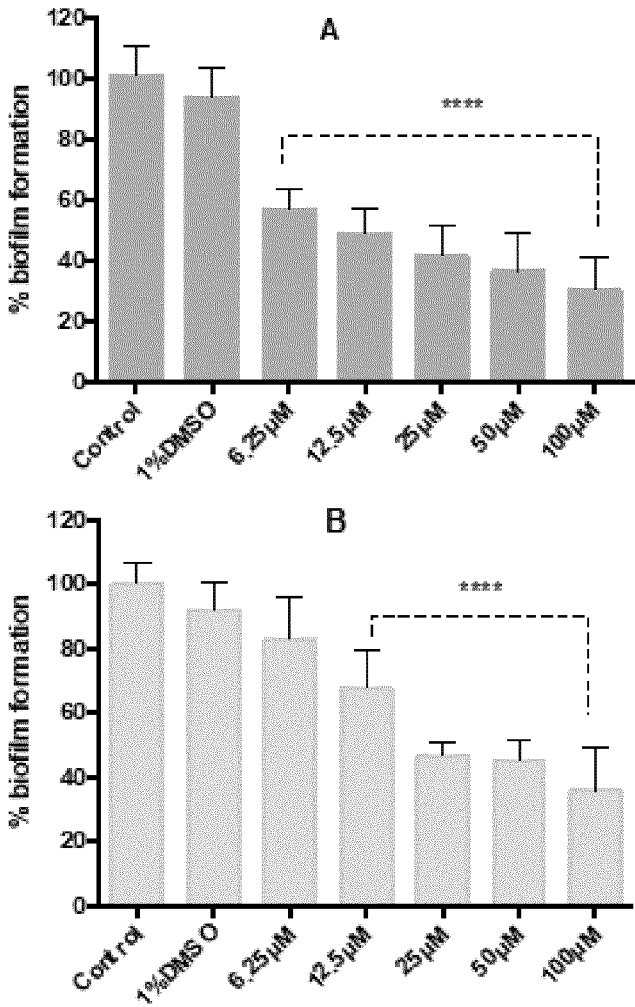
FIG. 1: The effect of varying concentrations of DHA on the ability of *Klebsiella pneumoniae* NCIMB 418 (A) and *Enterococcus faecalis* ATCC 7080 (B) to form a biofilm in vitro. ($10^6$ CFU/well was incubated with various concentrations of DHA in a 96 well plate for 24 hours statically at 37° C. Biofilm formation was assessed using the crystal violet assay. Data represents the mean±SD for six independent experiments, carried out in triplicate. One-way ANOVA was performed for statistical analysis. *****P<0.001 compared to both the control (no DHA) and vehicle control (1% DMSO).

Biofilms are notoriously difficult to remove or disrupt. The current inventors have surprising found that DHA possesses strong anti-biofilm effects against *Klebsiella pneumoniae* and against *Enterococcus faecalis*. This provides an effective means to treat *Klebsiella pneumoniae* or *Enterococcus faecalis* biofilms in vivo in a subject. Biofilms often occur in subjects because of contaminated medical devices for implantation and can cause lung infections and/or skin infections, for example.

When used in conjunction with an antibiotic, such as erythromycin, the combination was particularly effective at reducing biofilms containing these strains than either treatment on its own. This is particularly surprising as many bacteria are resistant to erythromycin.

Accordingly, the invention provides DHA, or a derivative thereof, for use in the treatment or prevention of a biofilm comprising *Klebsiella pneumoniae* and/or *Enterococcus faecalis* in a subject.

Preferably, DHA is a composition comprising DHA. The composition may be a pharmaceutical composition. The composition may have one or more pharmaceutically excipients.

The amount of DHA may be an effective amount to treatment the biofilm in a subject. The concentration of DHA used in the method may be from 1 µM to 500 µM, preferably from 1 µM to 200 µM, from 5 µM to 150 µM, from 6 µM to 100 µM, or from 10 µM to 90 µM, from 20 µM to 80 µM, from 30 µM to 70 µM, from 40 µM to 60 µM or 50 µM. Notably, the amount of DHA may be 6.25 µM to 100 µM, or 12.5 µM to 50 or 25 µM.

DHA may be in any suitable formulation. For example, a liquid formulation, powder, or tablet formulation.

Typically, DHA is one with an isotopic purity of ≥90% atom % D or ≥95% or ≥98%. Typically, it is one with an isotopic purity of ≥98%.

Notably, the method further comprises administration of an antibiotic to the subject. Administration may be simultaneous, or sequentially. For example, the subject may receive DHA first and subsequently receive an antibiotic. Alternatively, the subject may receive DHA and the antibiotic at the same time. In an embodiment, the antibiotic is a macrolide. The antibiotic may be one or more of the group comprising azithromycin, clarithromycin, erythromycin and roxithromycin. Preferably, the antibiotic is erythromycin. The amount of antibiotic may be any suitable amount.

DHA and the antibiotic may be in one composition or may be in separate compositions.

The subject may be any subject in need of treatment. The subject may be a patient in a hospital, for example an immunocompromised subject. The subject may be one with cystic fibrosis or Crohn's disease. The subject may be one suspect of having, or at risk of having, formation of a biofilm comprising *Klebsiella pneumoniae* and/or *Enterococcus faecalis*. The subject may be one having, suspected of having, or at risk of having, one or more diseases associated with *Klebsiella pneumoniae* and/or *Enterococcus faecalis*.

The biofilm may be at any location in the subject. For example, in the lung, the heart, e.g. a cardiac biofilm, eye, urinary tract, the gastrointestinal tract and the skin.

The subject may be one with an implanted or indwelling medical device. The medical device may be selected from the group comprising but not limited to prosthetic heart valves, orthopaedic implants, intravascular catheters, artificial hearts, left ventricular assist devices, cardiac pacemakers, defibrillator, vascular prostheses, cerebrospinal fluid shunts, urinary catheters, ocular prostheses and contact lenses, and intrauterine contraceptive device. The medical device may be an indwelling medical device.

In an embodiment, the subject may receive DHA and/or the antibiotic as a prophylactic in a subject. In such an embodiment, the subject may be one that will undergo surgery, e.g. to receive an implanted medical device or stem cells, or the subject may be an immunocompromised subject.

The biofilm may be one formed on an implanted or indwelling medical device.

The biofilm may comprise (or consist of) *Klebsiella pneumoniae* and *Enterococcus faecalis*. The biofilm may comprise (or consist) of *Klebsiella pneumoniae*. The biofilm may comprise (or consist) of *Enterococcus faecalis*.

The biofilm comprising *Klebsiella pneumoniae* and/or *Enterococcus faecalis* in a subject may be one associated with a disease caused by *Klebsiella pneumoniae* and/or *Enterococcus faecalis* as described herein. The biofilm may comprise (or consist) of *Klebsiella pneumoniae*

Notably, the invention provides DHA for use in a method of treatment or prevention of a disease or infection associated with *Klebsiella pneumoniae* or *Enterococcus faecalis* biofilm formation in a subject. Preferably, the DNA is administered in the method in combination with an antibiotic, preferably erythromycin.

The disease may be one or more associated with or caused by *Klebsiella pneumoniae*, selected from the group comprising *pneumoniae*, urinary tract infection (UTI), a wound or surgical site infection, intra-abdominal infection, bloodstream infection (BSI), meningitis, and pyogenic liver abscess.

The disease may be one or more associated with or caused by *Enterococcus faecalis*, selected from the group comprising *pneumoniae*, bacteraemia, endocarditis, urinary tract infection (UTI), periodontitis, a wound or surgical site infection, intra-abdominal infection, bloodstream infection (BSI), meningitis, and pyogenic liver abscess.

Typically, the disease is one acquired in a clinical setting. The clinical settling may be a hospital, or clinic, a doctor or consultant surgery. It may also include extended care facilities, ambulatory surgical units home healthcare sites and other healthcare settings.

The embodiments of this aspect of the invention are as described in relation to the first aspect of the invention. DHA is one as described herein in relation to the first aspect of the invention.

It will be appreciated that a person skilled in the art would be capable of determining an appropriate dose of the DHA or compositions of the invention, or antibiotic, to administer without undue experimentation. Alternatively, a physician will determine the actual dose that is most suitable for a patient depending on the particular condition, disease or disorder to be treated or cared for and the age, body weight and/or health of the person. It will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. There can, of course, be individual instances where higher or lower dosage ranges are merited, and such are within the scope of this invention. The amount and the frequency are as best suited to the purpose. The frequency of application or administration can vary greatly, depending on the needs of each subject, with a recommendation of an application or administration range from once a month to ten times a day, preferably from once a week to four times a day, more preferably from three times a week to three times a day, even more preferably once or twice a day.

Compositions may be formulated in unit dosage form, i.e., in the form of discrete portions containing a unit dose, or a multiple or sub-unit of a unit dose.

It will be appreciated that the embodiments described in relation to one aspect of the invention may also apply to other aspects of the invention.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Example 1

Evaluating DHA for anti-biofilm effects against *Klebsiella pneumoniae* NCIMB 418 and *Enterococcus faecalis* ATCC 7080

Methodology

The effect of varying concentrations of DHA on the ability of *Klebsiella pneumoniae* NCIMB 418 and *Enterococcus faecalis* ATCC 7080 to form a biofilm in vitro was investigated. $10^6$ CFU/well was incubated with various concentrations of DHA in a 96 well plate for 24 hours statically at 37° C. Biofilm formation was assessed using the crystal violet assay. Data represents the mean±SD for six independent experiments, carried out in triplicate. The assay involves seeding cells at $10^{\wedge 6}$ CFU/ml in media with DHA. Cells were then left for 24 hrs to form biofilms before washing and staining with Crystal Violet. Crystal violet adheres to cells stuck to the sides of the tube/well. The samples is washed again to remove any unbound dye before dissolving the stain in acetic acid and measuring the reading in a spectrophotometer. The colour intensity relates to the level of biofilm present. The more colour the more bacteria in the biofilm. Merritt, J. H., Kadouri, D. E. and O'Toole, G. A. (2005) 'Growing and Analyzing Static Biofilms', *Current Protocols in Microbiology*, Chapter 1(Jul), p. Unit 1B.1.

Results

As shown in FIG. 1A an anti-biofilm effect was seen against of *Klebsiella pneumoniae* NCIMB 418 with DHA versus control at concentrations between 6.25 μM (~40% reduction) and 100 μM (~65% reduction).

As show in FIG. 1 6 an anti-biofilm effect was seen against *Enterococcus faecalis* ATCC 7080 with DHA versus control at concentrations between 6.25 μM (~20% reduction) and 100 μM (~65% reduction).

Example 2

Evaluating Erythromycin in conjunction with DHA on the ability of *K. pneumoniae* NCIMB 418 to form biofilms in vitro.

Methodology

The effects of DHA (16 μM) and Erythromycin (4 μg/ml) were compared individually and adjunct for antibiofilm effects against *Klebsiella pneumoniae* NCIMB 481 in vitro. $10^6$ CFU/well was incubated with each well of a 96 well plate for 24 hours statically at 37° C. Biofilm formation was assessed using the crystal violet assay. Data represents the mean±SD for four independent experiments, carried out in triplicate.

Results

Figure 2:
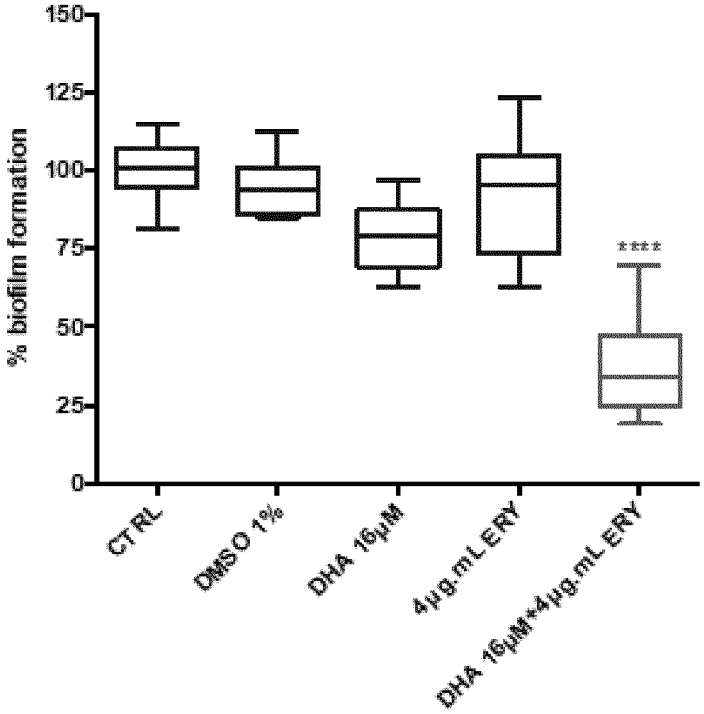
FIG. 2: Comparing DNA (16 μM) and Erythromycin (4 μg/ml) individually and adjunct for antibiofilm effects against *Klebsiella pneumoniae* NCIMB 481 in vitro. $10^6$ CFU/well was incubated with each well of a 96 well plate for 24 hours statically at 37° C. Biofilm formation was assessed using the crystal violet assay. Data represents the mean±SD for four independent experiments, carried out in triplicate. One-way ANOVA was performed for statistical analysis. *****P<0.001 compared to both the control (no DHA or Erythromycin), vehicle control (1% DMSO), DHA (16 μM) and Erythromycin (4 μg·mL).
Figure 3:
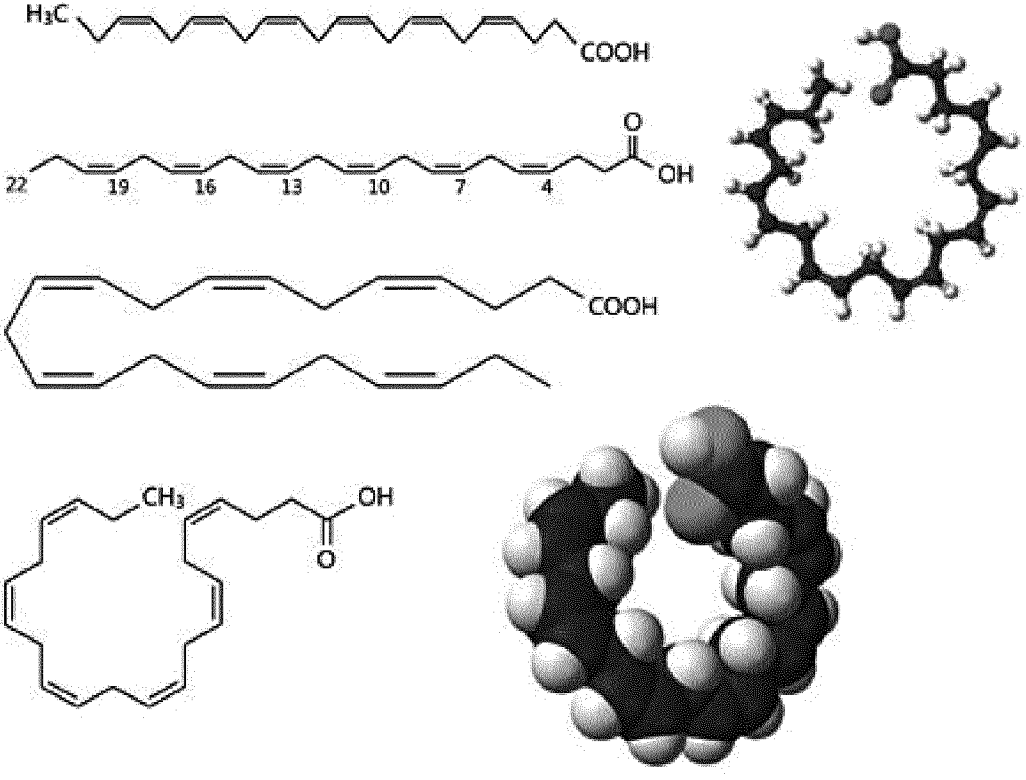
FIG. 3: DHA chemical structure.

As shown in FIG. 2 the combination of DHA and Erythromycin reduced biofilm formation by about 75%. This is a greater reduction that either agent used alone.

It will be appreciated that this method can be repeated to evaluate any antibiotic, such as any macrolide antibiotic, in combination with DHA.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method of treatment of a biofilm comprising *Klebsiella pneumoniae* and/or *Enterococcus faecalis* in a subject, the method comprising:

administering:

a) an effective amount of DHA or a derivative thereof, and b) a macrolide antibiotic;

to the subject.

2. The method of claim 1, wherein the macrolide antibiotic is selected from azithromycin, clarithromycin, erythromycin, and roxithromycin.

3. The method of claim 1, wherein the subject is one with an implanted or indwelling medical device, or an immuno-compromised subject, or a subject that will undergo surgery to receive an implanted or indwelling medical device.

4. The method of claim 1 wherein the subject is one with an implanted or indwelling medical device, or a subject that will undergo surgery to receive an implanted or indwelling medical device, and wherein the medical device is selected from the group consisting of:

prosthetic heart valves, orthopaedic implants, intravascular catheters, artificial hearts, left ventricular assist devices, cardiac pacemakers, defibrillator, vascular prostheses, cerebrospinal fluid shunts, urinary catheters, ocular prostheses, contact lenses, and intrauterine contraceptive device.

5. The method of claim 1, wherein the DHA is in the form of a pharmaceutical composition comprising DHA and one or more pharmaceutically acceptable excipients.

6. The method of claim 1, wherein the concentration of the DHA is from 1 μM to 200 μM.

7. The method of claim 1 wherein the concentration of the DHA is from 6 μM to 100 μM.

8. The method of claim 1, wherein the biofilm is one in the lung, the heart, the skin, the eye, the gastrointestinal tract, and/or the urinary tract of the subject.

9. The method of claim 1, wherein the DHA and the macrolide antibiotic are administered simultaneously.

10. The method of claim 1, wherein when the DHA and the macrolide antibiotic are administered in one composition.

11. The method of claim 1, wherein the macrolide antibiotic is erythromycin.

12. The method of claim 1, wherein the DNA and the macrolide antibiotic are administered sequentially.

13. The method of claim 1, wherein when the DHA and macrolide antibiotic are administered in separate compositions.

14. A method of treatment of a disease or condition associated with *Klebsiella pneumoniae* or *Enterococcus faecalis* biofilm formation in a subject, comprising administration of n DHA and a macrolide antibiotic to the subject.

15. The method of claim 14, wherein the macrolide antibiotic is selected from azithromycin, clarithromycin, erythromycin, and roxithromycin.

16. The method of claim 14, wherein the DHA and the macrolide antibiotic are administered simultaneously.

17. The method of claim 14, wherein when the DHA and the macrolide antibiotic are administered in one composition.

18. The method of claim 14, wherein the DNA and the macrolide antibiotic are administered sequentially.

19. The method of claim 14, wherein when the DHA and macrolide antibiotic are administered in separate compositions.

* * * * *